United States Patent
Allen, IV

(10) Patent No.: US 11,090,099 B2
(45) Date of Patent: Aug. 17, 2021

(54) SURGICAL FORCEPS AND METHODS OF MANUFACTURING THE SAME

(71) Applicant: COVIDIEN LP, Mansfield, MA (US)

(72) Inventor: James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 351 days.

(21) Appl. No.: 15/946,366

(22) Filed: Apr. 5, 2018

(65) Prior Publication Data

US 2018/0221076 A1  Aug. 9, 2018

Related U.S. Application Data

(63) Continuation of application No. 14/722,769, filed on May 27, 2015, now Pat. No. 9,956,022.

(51) Int. Cl.
| | |
|---|---|
| *A61B 18/00* | (2006.01) |
| *A61B 18/14* | (2006.01) |
| *A61B 17/29* | (2006.01) |

(52) U.S. Cl.
CPC .............. *A61B 18/00* (2013.01); *A61B 17/29* (2013.01); *A61B 18/1445* (2013.01);
(Continued)

(58) Field of Classification Search
CPC ..... A61B 17/29; A61B 18/00; A61B 18/1445; A61B 2017/02934; A61B 2017/2936; A61B 2017/2937
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| | (Continued) | |

FOREIGN PATENT DOCUMENTS

| | | |
|---|---|---|
| CN | 201299462 Y | 9/2009 |
| DE | 2415263 A1 | 10/1975 |
| | (Continued) | |

OTHER PUBLICATIONS

U.S. Appl. No. 14/098,953, filed Dec. 6, 2013; inventor: Cunningham.
(Continued)

*Primary Examiner* — Daniel W Fowler
*Assistant Examiner* — Tigist S Demie
(74) *Attorney, Agent, or Firm* — Carter, DeLuca & Farrell LLP

(57) ABSTRACT

A forceps includes a shaft defining first opposed distal recesses, a drive bar slidably disposed within the shaft and defining second opposed distal recesses, and an end effector assembly including first and second jaw members. Each jaw member defines a proximal flange and a distal jaw body. The proximal flanges each define an aperture and a cam slot. A pivot pin extends through the apertures with ends of the pivot pin extending outwardly from the jaw members to be at least partially disposed within the first recesses and fixedly engaged therewith. A drive pin extends through the cam slots with ends of the drive pin extending outwardly from the jaw members to be at least partially disposed within the second recesses and fixedly engaged therewith such that translation of the drive bar relative to the end effector assembly pivots the jaw members between spaced-apart and approximated positions.

14 Claims, 6 Drawing Sheets

(52) U.S. Cl.
CPC .............. *A61B 2017/2934* (2013.01); *A61B 2017/2936* (2013.01); *A61B 2017/2937* (2013.01)

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H001745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H001904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H002037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,628,792 B2 | 12/2009 | Guerra |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| 7,837,631 B2 | 11/2010 | Diamond et al. |
| 7,842,045 B2 | 11/2010 | Vandenbroek |
| D630,324 S | 1/2011 | Reschke |
| 7,935,052 B2 | 5/2011 | Dumbauld |
| D649,249 S | 11/2011 | Guerra |
| D649,643 S | 11/2011 | Allen, IV et al. |
| 8,133,254 B2 | 3/2012 | Dumbauld et al. |
| D661,394 S | 6/2012 | Romero et al. |
| D670,808 S | 11/2012 | Moua et al. |
| D680,220 S | 4/2013 | Rachlin |
| 8,491,625 B2 | 7/2013 | Horner |
| 8,636,761 B2 | 1/2014 | Cunningham et al. |
| 2012/0101484 A1 | 4/2012 | Miersch |
| 2013/0046303 A1 | 2/2013 | Evans et al. |
| 2013/0066230 A1 | 3/2013 | Li et al. |
| 2013/0085516 A1 | 4/2013 | Kerr et al. |
| 2013/0296848 A1 | 11/2013 | Allen, IV et al. |
| 2014/0025070 A1* | 1/2014 | Kerr ................... A61B 17/295 606/45 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 | 9/1984 |
| JP | 1024051 A | 1/1989 |
| JP | 1147150 A | 6/1989 |
| JP | 6502328 | 3/1992 |
| JP | 55106 | 1/1993 |
| JP | 0540112 | 2/1993 |
| JP | 0006030945 A | 2/1994 |
| JP | 6121797 A | 5/1994 |
| JP | 6285078 A | 10/1994 |
| JP | 06343644 A | 12/1994 |
| JP | 6511401 | 12/1994 |
| JP | 07265328 A | 10/1995 |
| JP | 856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 910223 C | 1/1997 |
| JP | 09000538 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | 11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 A | 1/2001 |
| JP | 2001029355 | 2/2001 |
| JP | 2001029356 A | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |

(56) References Cited

FOREIGN PATENT DOCUMENTS

| | | |
|---|---|---|
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Heniford et al. "Initial Research and Clinical Results with an Electrothermal Bipolar Vessel Sealer" Oct. 1999.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. Jan. 1, 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 1, 2001; pp. 21-24.

(56) References Cited

OTHER PUBLICATIONS

Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremeich.
U.S. Appl. No. 14/065,644, filed Oct. 29, 2013; inventor: Reschke.

\* cited by examiner

SURGICAL FORCEPS AND METHODS OF MANUFACTURING THE SAME

CROSS-REFERENCE TO RELATED APPLICATIONS

Technical Field

This application is a continuation of U.S. patent application Ser. No. 14/722,769, filed on May 27, 2015, the entire contents of which are hereby incorporated by reference herein.

BACKGROUND

Technical Field

The present disclosure relates to surgical instruments and, more particularly, to surgical forceps configured for treating tissue, and methods of manufacturing the same.

Background of Related Art

A surgical forceps is a plier-like device which relies on mechanical action between its jaws to grasp, clamp, and constrict tissue. Energy-based surgical forceps utilize both mechanical clamping action and energy to treat, e.g., coagulate, cauterize, and/or seal, tissue.

Generally, surgical instruments, including surgical forceps, can be classified as disposable instruments, e.g., instruments that are discarded after a single use, or reusable instruments, e.g., instruments capable of being sterilized for repeated use. As can be appreciated, those instruments that are configured for single-use must be cost-efficient while still being capable of effectively performing their intended functions.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A forceps provided in accordance with aspects of the present disclosure includes a shaft including opposed first recesses defined at a distal end thereof, a drive bar slidably disposed within the shaft and including opposed second recesses defined at a distal end thereof, and an end effector assembly including first and second jaw members. Each of the first and second jaw members includes a proximal flange and a distal jaw body extending distally from the proximal flange. The proximal flange of each of the first and second jaw members includes a transverse aperture and a cam slot defined therein. A pivot pin extends through the transverse apertures of the first and second jaw members with ends of the pivot pin extending outwardly from the proximal flanges of the first and second jaw members. The ends of the pivot pin are at least partially disposed within the first recesses of the shaft and fixedly engaged therewith. A drive pin extends through the cam slots of the first and second jaw members with ends of the drive pin extend outwardly from the proximal flanges of the first and second jaw members. The ends of the drive pin are at least partially disposed within the second recesses of the drive bar and fixedly engaged therewith such that translation of the drive bar relative to the end effector assembly urges the drive pin through the cam slots, thereby pivoting the first and second jaw members about the pivot pin between a spaced-apart position and an approximated position.

In an aspect of the present disclosure, the ends of the pivot pin are welded at least partially within the first recesses of the shaft. Additionally or alternatively, the ends of the drive pin may be welded at least partially within the second recesses of the drive bar.

In another aspect of the present disclosure, the distal jaw bodies of the first and second jaw members include tissue-treating surfaces configured to grasp tissue therebetween in the approximated position of the first and second jaw members. The tissue-treating surfaces may be configured to conduct energy through tissue grasped therebetween to treat tissue.

In yet another aspect of the present disclosure, the forceps further includes a housing having the shaft extending distally therefrom and a handle assembly coupled to the housing and the drive bar. The handle assembly includes a movable handle selectively actuatable for translating the drive bar through the shaft.

In still another aspect of the present disclosure, the first recesses are at least partially complementary in shape to the pivot pin. Additionally or alternatively, the second recesses may be at least partially complementary in shape to the drive pin.

Another forceps provided in accordance with aspects of the present disclosure includes a shaft including a first inwardly-extending lip at a distal end thereof, and an end effector assembly including first and second jaw members. The first jaw member includes a first proximal flange and a first distal jaw body extending distally from the first proximal flange. The first proximal flange includes a first notch configured to at least partially receive the first lip to define a fulcrum about which the first jaw member is pivotable relative to the second jaw member and the shaft between a spaced-apart position relative to the second jaw member and an approximated position relative to the second jaw member.

In an aspect of the present disclosure, a drive bar is slidably disposed within the shaft. The drive bar includes a transverse drive pin disposed at a distal end thereof. The first proximal flange further includes a cam slot therethrough with the transverse drive pin operably engaged within the cam slot such that translation of the drive bar relative to the shaft pivots the first and second jaw members between the spaced-apart and approximated positions.

In another aspect of the present disclosure, the operable engagement of the transverse drive pin within the cam slot retains the first lip at least partially within the first notch.

In still another aspect of the present disclosure, the forceps further includes a housing having the shaft extending distally therefrom and a handle assembly coupled to the housing and the drive bar. The handle assembly includes a movable handle selectively actuatable for translating the drive bar through the shaft.

In yet another aspect of the present disclosure, the shaft includes a second inwardly-extending lip at the distal end thereof and the second jaw member includes a second proximal flange and a second distal jaw body extending distally from the second proximal flange. The second proximal flange includes a second notch defined therein and configured to at least partially receive the second lip to define a fulcrum about which the second jaw member is pivotable relative to the first jaw member and the shaft between the spaced-apart position and the approximated position.

In still yet another aspect of the present disclosure, the first and second distal jaw bodies of the first and second jaw members include first and second tissue-treating surface configured to grasp tissue therebetween in the approximated position of the first and second jaw members. The first and second tissue-treating surfaces may be configured to conduct energy through tissue grasped therebetween to treat tissue.

Another forceps provided in accordance with aspects of the present disclosure includes a shaft, a drive bar slidably disposed within the shaft and including a transverse drive pin engaged thereto towards a distal end thereof, and an end effector assembly including first and second jaw members. The first and second jaw members include respective first and second proximal flanges and respective first and second distal jaw bodies extending distally from the first and second proximal flanges. The first and second proximal flanges are fixedly engaged with the shaft at a distal end of the shaft. The first jaw member includes a living hinge interconnecting the first proximal flange and the first distal jaw body so as to permit deflection of the first distal jaw body relative to the first proximal flange and the shaft. The first jaw member further includes a first upright and a first slot defined between the first upright and the first proximal flange. The first slot is configured to at least partially receive the transverse drive pin such that translation of the drive bar relative to the end effector assembly urges the transverse drive pin into contact with the first upright, thereby deflecting the first distal jaw body relative to the shaft and the second distal jaw body from an approximated position to a spaced-apart position.

In an aspect of the present disclosure, the second distal jaw body is rigidly engaged with the second proximal flange. Alternatively, the second jaw member may include a living hinge interconnecting the second proximal flange and the second distal jaw body and may be configured similarly to the first jaw member, as detailed above.

In another aspect of the present disclosure, the first and second distal jaw bodies of the first and second jaw members define first and second tissue-treating surface configured to grasp tissue therebetween in the approximated position. The first and second tissue-treating surfaces may be configured to conduct energy through tissue grasped therebetween to treat tissue.

BRIEF DESCRIPTION OF THE DRAWINGS

Various aspects and features of the present disclosure described herein with reference to the drawings wherein.

DETAILED DESCRIPTION

Figure 1:
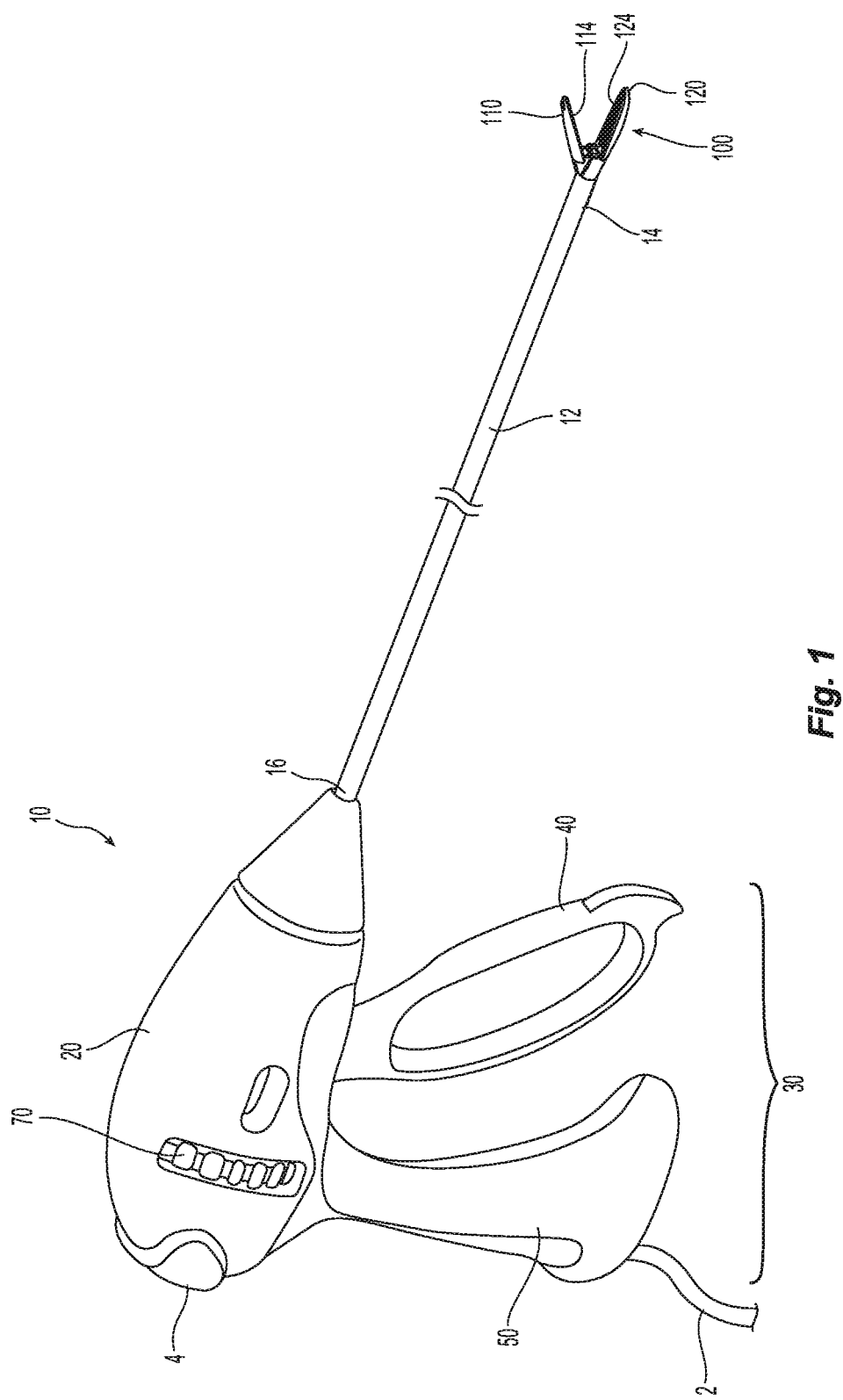
FIG. 1 is a perspective view of an endoscopic surgical forceps provided in accordance with the present disclosure.

Referring to FIG. 1, an embodiment of a surgical forceps provided in accordance with the present disclosure is shown generally identified by reference numeral 10. Although surgical forceps 10 is shown configured for use in connection with endoscopic surgical procedures, the present disclosure is equally applicable for use in more traditional open surgical procedures and with any suitable surgical instrument.

Forceps 10 generally includes a housing 20, a handle assembly 30, a rotating assembly 70, an activation switch 4, and an end effector assembly 100. Forceps 10 further includes a shaft 12 having a distal end 14 configured to engage end effector assembly 100 and a proximal end 16 that engages housing 20. Opposed recesses 18 (FIG. 3A) defined within shaft 12 at distal end 14 thereof are configured to facilitate engagement of end effector assembly 100 with shaft 12, as detailed below.

Forceps 10 also includes cable 2 that connects forceps 10 to an energy source (not shown), e.g., a generator or other suitable power source, although forceps 10 may alternatively be configured as a battery-powered device. Cable 2 includes a wire (or wires) (not shown) extending therethrough that has sufficient length to extend through shaft 12 in order to provide energy to one or both tissue-treating surfaces 114, 124 of jaw members 110, 120, respectively. Activation switch 4 is coupled between tissue-treating surfaces 114, 124 of jaw members 110, 120, respectively, and the source of energy for enabling the selective supply of energy to jaw members 110, 120 for treating tissue grasped therebetween. Rotating assembly 70 is rotatable in either direction to rotate end effector assembly 100 relative to housing 20.

Figure 2:
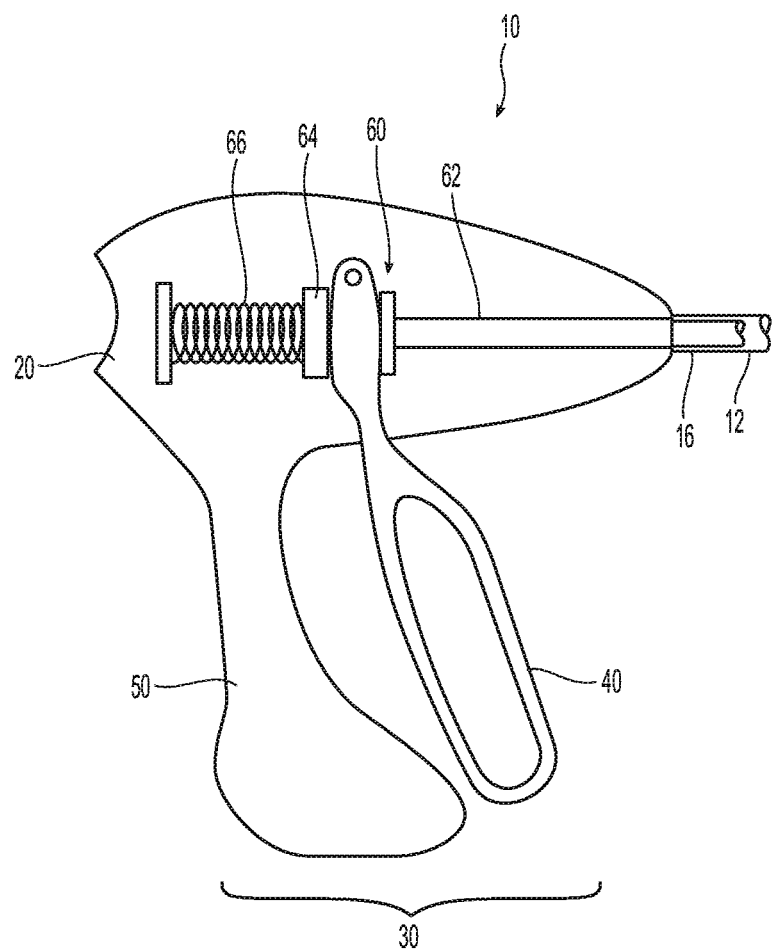
FIG. 2 is a side view of the proximal end of the forceps of FIG. 1, with a portion of the housing removed to enable illustration of the internal features thereof.

With additional reference to FIG. 2, handle assembly 30 includes a fixed handle 50 and a movable handle 40. Fixed handle 50 is integrally associated with housing 20 while movable handle 40 is pivotably coupled to housing 20 within housing 20 via a pivot 42. Movable handle 40 is also operably coupled to a drive assembly 60 operably associated with end effector assembly 100 that, together, mechanically cooperate to impart movement of one or both of jaw members 110, 120 of end effector assembly 100 relative to each other between a spaced-apart position and an approximated position for grasping tissue therebetween. More specifically, movable handle 40 is coupled to a drive bar 62 via a drive mandrel 64 such that movement of movable handle 40 relative to fixed handle 50 effects longitudinal translation of drive bar 62 through shaft 12 and relative to end effector assembly 100. The distal end of drive bar 62 is configured to engage one or both jaw members 110, 120 such that longitudinal translation of drive bar 62 relative to end effector assembly 100 pivots one or both of jaw members 110, 120 between the spaced-apart position and the approximated position. Opposed recesses 68 (FIG. 3A) defined within drive bar 62 at the distal end thereof are configured to facilitate engagement of end effector assembly 100 with drive bar 62, as detailed below.

As shown in FIGS. 1 and 2, movable handle 40 is initially spaced-apart from fixed handle 50 and, correspondingly, jaw members 110, 120 are disposed in the spaced-apart position. Movable handle 40 is depressible from this initial position to a depressed position corresponding to the approximated position of jaw members 110, 120. A biasing member 66 may be disposed about drive bar 62 and positioned to bias jaw members 110, 120 towards the spaced-apart position and movable handle 40 apart from fixed handle 50. However, other configurations are also contemplated.

Figure 3A:
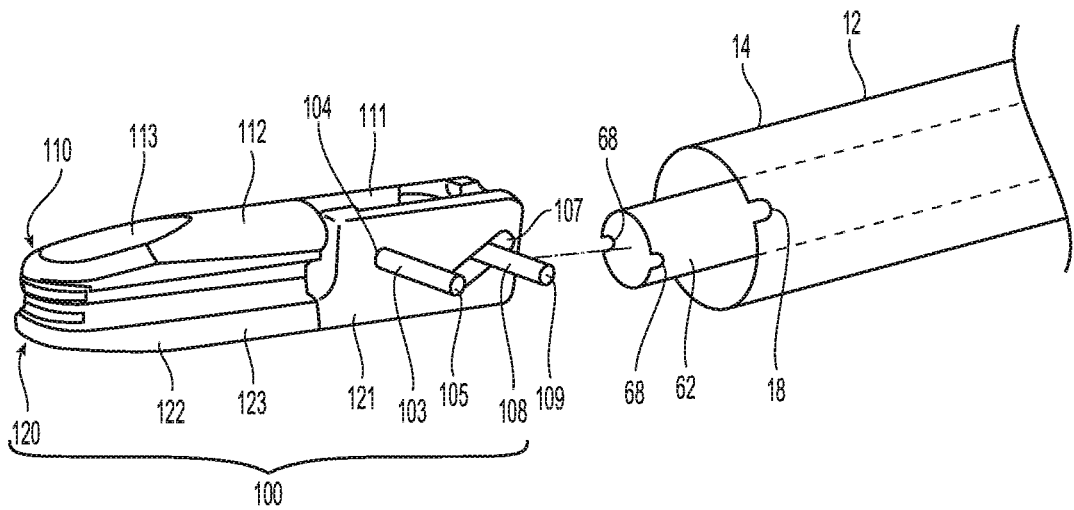
FIG. 3A is an exploded, perspective view of the distal end of the forceps of FIG. 1 prior to engagement of an end effector assembly with a shaft and drive assembly.
Figure 3B:
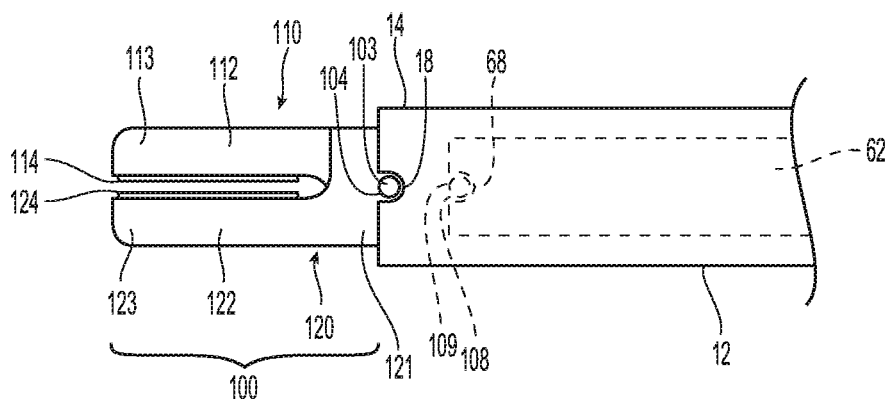
FIG. 3B is a side view of the distal end of the forceps of FIG. 1 after engagement of the end effector assembly with the shaft and drive assembly.

Referring to FIGS. 3A and 3B, in conjunction with FIGS. 1 and 2, end effector assembly 100 includes first and second jaw members 110, 120, each including a proximal flange 111, 121 and a distal jaw body 112, 122 including an outer insulative jaw housing 113, 123 and a tissue-treating surface 114, 124, respectively. Proximal flanges 111, 121 are pivotably coupled to one another via a pivot pin 103 extending through transverse apertures 104 (only aperture 104 of proximal flange 121 of jaw member 120 is illustrated) defined within proximal flanges 111, 121. Ends 105 of pivot pin 103 (only one end 105 of pivot pin 103 is illustrated) extend outwardly from either side of proximal flanges 111, 121. As detailed below, ends 105 of pivot pin 103 are engaged with distal end 14 of shaft 12 during manufacturing to thereby operably couple end effector assembly 100 with distal end 14 of shaft 12.

Either or both proximal flanges 111, 121 of jaw members 110, 120 further defines an angled cam slot 107 (only cam slot 107 of proximal flange 121 of jaw member 120 is illustrated). A drive pin 108 extends through cam slot(s) 107 in slidable and rotatable engagement therewith. Ends 109 of drive pin 108 (only one end 109 of drive pin 108 is illustrated) extend outwardly from either side of proximal flanges 111, 121. As detailed below, ends 109 of drive pin 108 are engaged with drive bar 62 of drive assembly 60 during manufacturing to thereby operably couple end effector assembly 100 with drive assembly 60. More specifically, with drive bar 62 coupled with drive pin 108, longitudinal translation of drive bar 62 through shaft 12 and relative to end effector assembly 100, e.g., in response to actuation of movable handle 40, may be effected to pivot jaw members 110, 120 between the spaced-apart position and the approximated position.

End effector assembly 100 may be configured as a unilateral assembly, e.g., wherein one of the jaw members 110, 120 is fixed relative to shaft 12 and the other jaw member 110, 120 is movable relative to the fixed jaw member 110, 120 and shaft 12, or a bilateral assembly, e.g., wherein both jaw members 110, 120 are movable relative to one another and shaft 12. In unilateral configurations, pivot pin 103 and drive pin 108 are fixed to one of the jaw members 110, 120, while the other jaw member 110, 120 defines a transverse aperture 104 for rotatably receiving pivot pin 103 and a cam slot 107 for slidably and rotatably receiving drive pin 108. In bilateral configurations, both jaw members 110, 120 define transverse apertures 104 for rotatably receiving pivot pin 103 and oppositely-angled cam slots 107 for slidably and rotatably receiving drive pin 108.

Continuing with reference to FIGS. 3A and 3B, in conjunction with FIGS. 1 and 2, forceps 10 is configured such that end effector assembly 100 may initially be formed as a sub-unit, e.g., including jaw members 110, 120, pivot pin 103, and drive pin 108, which then may then be operably engaged with shaft 12 and drive bar 62. More specifically, as noted above, the assembled sub-unit of end effector assembly 100 is configured such that the ends 104, 109 of pivot pin 103 and drive pin 108, respectively, extend outwardly from either side of end effector assembly 100. As also noted above, distal end 14 of shaft 12 and the distal end of drive bar 62 define opposed recesses 18, 68, respectively. Recesses 18, 68 are configured to at least partially receive ends 104, 109 of pivot pin 103 and drive pin 108, respectively, on either side of end effector assembly 100. Recesses 18, 68 may define semi-circular configurations complementary to that of pivot pin 103 and drive pin 108, respectively, so as to define a semi-annular abutting region wherein the surfaces of shaft 12 and drive bar 62 which define respective recesses 18, 68 abut a half-circumference of the outer surface of the respective pin 103, 108.

The abutting surfaces between shaft 12 and pivot pin 103 and between drive bar 62 and drive pin 108 ensure proper alignment and orientation of end effector assembly 100 relative to shaft 12 and drive bar 62 and also provide a suitable surface area to facilitate welding, or otherwise engaging, pivot pin 103 within recess 18 of shaft 12 and drive pin 108 with recess 68 of drive bar 62. More specifically, the semi-circular abutment regions between shaft 12 and pivot pin 103 and between drive bar 62 and drive pin 108 maximizes the length of the weld line (and maximize the surface area contact for other forms of engagement), thus helping to ensure a sufficiently strong engagement between shaft 12 and pivot pin 103 and between drive pin 103e bar 62 and drive pin 108. Further, the need for complex manufacturing machinery and/or techniques is eliminated. Rather, end effector assembly 100 may be first formed as a sub-unit and then operably engaged with forceps 10 via welding (or otherwise engaging) pivot pin 103 at least partially within recesses 18 of shaft 12 and via welding (or otherwise engaging) drive pin 108 at least partially within recesses 68 of drive bar 62.

Figure 4A:
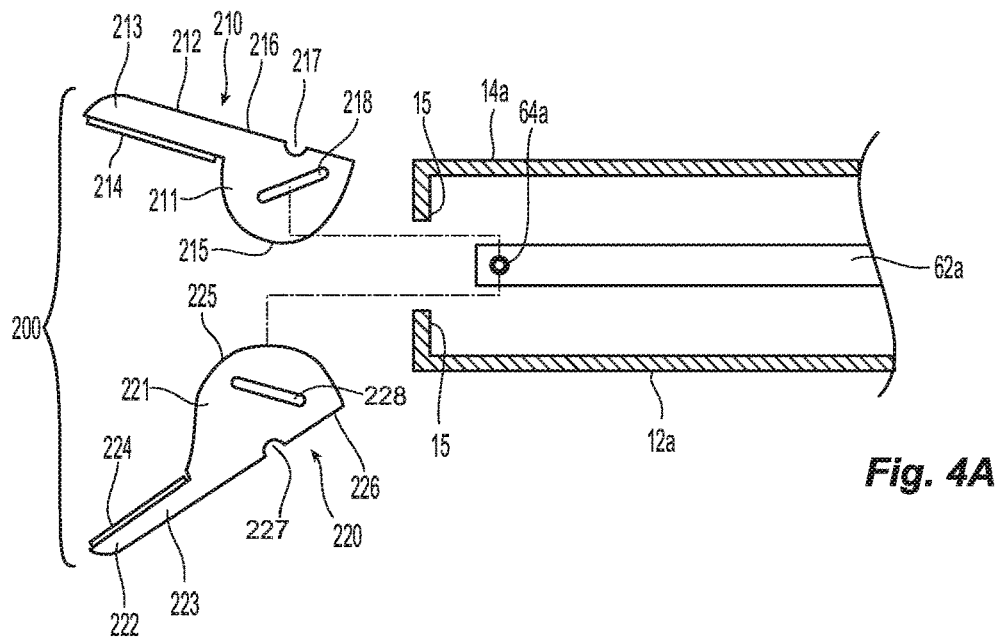
FIG. 4A is an exploded, longitudinal, cross-sectional view of the distal end of another forceps provided in accordance with the present disclosure, prior to engagement of the end effector assembly with the shaft and drive assembly.
Figure 4B:
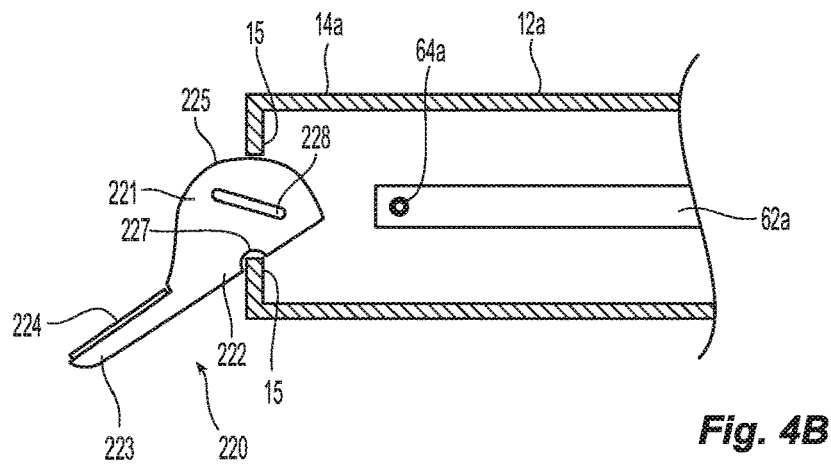
FIGS. 4B and 4C are longitudinal, cross-sectional views illustrating operable engagement of one of the jaw members of the end effector assembly of the forceps of FIG. 4A with the shaft and drive assembly of the forceps of FIG. 4A.
Figure 4C:
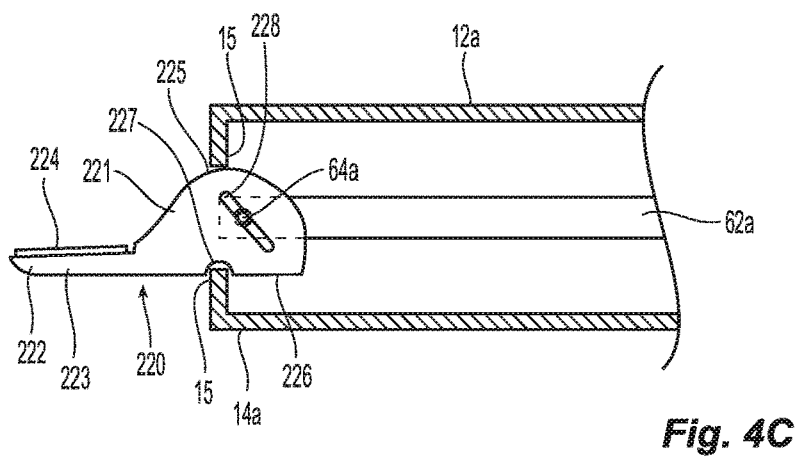

Turning to FIGS. 4A-4C, and with initial reference to FIG. 4A, another embodiment of an end effector assembly 200 provided in accordance with the present disclosure and configured for engagement with a shaft 12a and drive bar 62a of a forceps similar to forceps 10 (FIG. 1) is described. End effector assembly 200, similarly as with end effector assembly 100 (FIGS. 3A and 3B), includes first and second jaw members 210, 220, each including a proximal flange 211, 221 and a distal jaw body 212, 222 including an outer insulative jaw housing 213, 223 and a tissue-treating surface 214, 224, respectively. Proximal flanges 211, 221 define generally semi-circular configurations wherein each proximal flange 211, 221 defines an arcuate surface 215, 225 and a linear surface 216, 226. A notch 217, 227 is defined within each of proximal flanges 211, 221, respectively, and is positioned to at least partially interrupt respective linear surfaces 216, 226. Notches 217, 227 are configured to facilitate pivotable coupling of jaw members 210, 220 to shaft 12a, as detailed below. Proximal flanges 211, 221 further include oppositely-angled cam slots 218, 228, respectively, defined therethrough that are configured to facilitate operable engagement of jaw members 210, 220 with drive bar 62a, as will also be detailed below.

Shaft 12a defines an elongated tubular configuration having a hollow interior and may be formed in any suitable cross-sectional shape, e.g., circular, elliptical, rectangular, etc. Shaft 12a further defines, at distal end 14a thereof, a pair of opposed, inwardly-extending lips 15. Lips 15 may be formed separately from one another, or may be formed as different portions of a continuous lip extending inwardly from the perimeter of distal end 14a of shaft 12a. Each lip 15 serves as a fulcrum for operably supporting one of the proximal flanges 211, 221 of jaw members 210, 220, respectively. As an alternative to this bilateral configuration, shaft 12a may define a single lip 15 for operably supporting the proximal flange 211, 221 of one of the jaw members 210, 220, while the other jaw member 210, 220 is fixed relative to shaft 12a. Lips 15 may be formed with shaft 12a in any suitable manner, e.g., as part of the initial forming of shaft 12a, via bending and/or cutting distal end 14a of shaft 12a to form lips 15, via engaging lips 15 onto distal end 14a of shaft 12a, or in any other suitable fashion.

Drive bar 62a is slidably disposed within shaft 12a and is selectively translatable therethrough upon actuation of a handle assembly associated with the forceps, e.g., similarly as detailed above with respect to handle assembly 30 and drive assembly 60 of forceps 10 (FIGS. 1 and 2). Drive bar 62a includes a transverse drive pin 64a extending from either side thereof towards the distal end of drive bar 62a. Each end of transverse drive pin 64a is configured for receipt within one of the cam slots 218, 228 of proximal flanges 211, 221 of jaw members 210, 220, respectively.

Referring to FIG. 4B, the operable engagement of jaw member 220 with shaft 12a and drive bar 62a is detailed. Because the operable engagement of jaw member 210 (FIG. 4A) with shaft 12a and drive bar 62a is similar, such will not be detailed herein to avoid unnecessary repetition. As an alternative to this bilateral configuration, a unilateral configuration may be provided wherein only one jaw member 210, 220 is assembled with shaft 12a and drive bar 62a, while the other jaw member 210, 220 is fixedly secured to shaft 12a.

In order to operably engage jaw member 220 with shaft 12a and drive bar 62a, jaw member 220 is initially manipulated into position such that notch 227 at least partially receives one of the lips 15 defined at distal end 14a of shaft 12a. This coupling of lip 15 within notch 227 defines the fulcrum about which jaw member 220 is rotated relative to shaft 12a.

With additional reference to FIG. 4C, once the coupling of lip 15 within notch 227 has been achieved, jaw member 220 is rotated to move proximal flange 221 into or further into shaft 12a such that cam slot 228 of proximal flange 221 is positioned adjacent the distal end of drive bar 62a. Arcuate surface 225 of proximal flange 221 enables proximal flange 221 to be rotated in this manner, ultimately such that, as noted above, cam slot 228 of proximal flange 221 is positioned adjacent the distal end of drive bar 62a and, more specifically, adjacent one of the ends of transverse drive pin 64a. Once this position has been achieved, drive bar 62a and/or jaw member 220 may be manipulated so as to permit the adjacent end of transverse drive pin 64a to be at least partially inserted through cam slot 228 in rotatable and slidable engagement therewith. The engagement of drive pin 64a within cam slot 228 not only operably engages jaw member 220 with drive bar 62a but also serves to operably retain jaw member 220 at distal end 14a of shaft 12a in pivotable engagement therewith, e.g., via the coupling of lip 15 within notch 227.

As an alternative to the above, wherein jaw member 220 is first coupled with shaft 12a and then to drive bar 62a, drive bar 62a may first be extended to enable receipt of one of the ends of transverse pin 64a within cam slot 228. Thereafter, jaw member 220 may be manipulated such that notch 227 at least partially receives one of the lips 15, then rotated about the fulcrum defined via the coupling of lip 15 within notch 227 to move jaw member 220 into position wherein proximal flange 221 extends at least partially into shaft 12a. Similarly as detailed above, arcuate surface 225 of proximal flange 221 enables jaw member 220 to be rotated to achieve this position. Jaw member 210 (FIG. 4A) may be engaged in the same order as jaw member 220 or in the opposite order. Further, jaw member 220 may be completely engaged prior to engagement of jaw member 210 (FIG. 4A), or jaw members 210, 220 (FIG. 4A) may be engaged together, e.g., wherein each assembly step is performed for each jaw member 210, 220 (FIG. 4A) prior to moving on to the next assembly step.

Figure 5A:
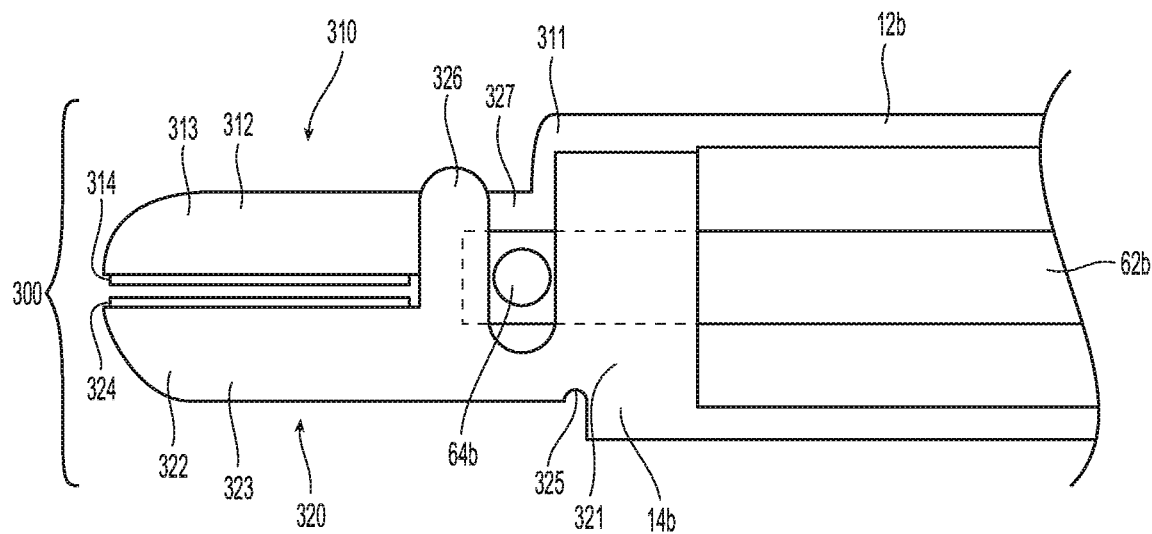
FIG. 5A is a longitudinal, cross-sectional view of the distal end of another forceps provided in accordance with the present disclosure, wherein jaw members of the forceps are disposed in an approximated position.
Figure 5B:
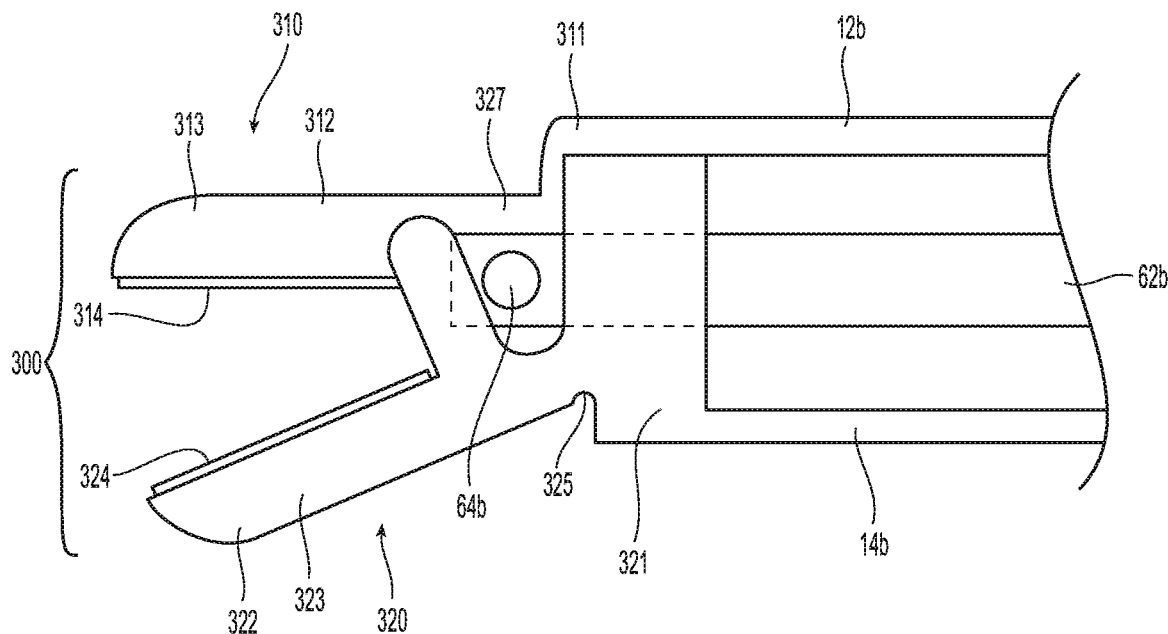
FIG. 5B is a longitudinal, cross-sectional view of the distal end of the forceps of FIG. 5A, wherein the jaw members are disposed in a spaced-apart position.

Turning to FIGS. 5A and 5B, another embodiment of an end effector assembly 300 of a forceps having a shaft 12b and drive bar 62b, similar to forceps 10 (FIG. 1), is provided in accordance with the present disclosure and described below. End effector assembly 300, similarly as with end effector assembly 100 (FIGS. 3A and 3B), includes first and second jaw members 310, 320, each including a proximal flange 311, 321 and a distal jaw body 312, 322 including an outer insulative jaw housing 313, 323 and a tissue-treating surface 314, 324, respectively. Proximal flanges 311, 321 are fixedly engaged with distal end 14b of shaft 12b, e.g., via welding, adhesion, mechanical fastening, via formation as a single component, etc., on opposed sides thereof. Distal jaw bodies 312, 322 of jaw members 310, 320, respectively, extend distally from proximal flanges 311, 321 and shaft 12b. Drive bar 62b includes a transverse drive pin 64b extending from either side thereof towards the distal end of drive bar 62b.

End effector assembly 300 may be configured as a unilateral assembly, wherein one of the jaw members 310, 320, e.g., jaw member 310, is configured such that distal jaw body 312 thereof is rigidly formed with proximal flange 311 thereof and, thus, shaft 12b, while the other jaw member 320 includes a living hinge 325 interconnecting distal jaw body 322 thereof and proximal flange 321 thereof, thus permitting deflection of distal jaw body 322 of jaw member 320 relative to proximal flange 321, shaft 12b, and distal jaw body 312 of jaw member 310. Alternatively, end effector assembly 300 may define a bilateral configuration, wherein both jaw members 310, 320 are configured to deflect relative to one another and shaft 12b. In such embodiments, jaw member 310 is configured similarly as jaw member 320, as detailed below.

Jaw member 320, as noted above, includes living hinge 325 interconnecting distal jaw body 322 and proximal flange 321. Living hinge 325 is resilient and biases jaw member 320 towards jaw member 310, the approximated position of end effector assembly 300 (FIG. 5A), although jaw member 320 may alternatively be biased towards the spaced-apart position relative to jaw member 310 (FIG. 5B). Jaw member 320 further includes an upright 326 positioned distally of living hinge 325 and a vertical slot 327 defined between upright 326 and proximal flange 321. Transverse drive pin 64b of drive bar 62b extends at least partially through vertical slot 327 and, thus is disposed at least partially between upright 326 and proximal flange 321. As a result of this configuration, when drive bar 62b is translated distally relative to shaft 12b and end effector assembly 300, transverse drive pin 64b is urged into contact with upright 326, ultimately such that upright 326 and distal jaw body 322 are urged to deflect relative to proximal flange 321 via flexion of living hinge 325, thereby moving distal jaw body 322 to the spaced-apart position relative to distal jaw body 312 of jaw member 310 (FIG. 5B). On the other hand, when drive bar 62b is translated proximally, transverse drive pin 64b no longer urges upright 326 to deflect, thus permitting jaw member 320 to return to the approximated position relative to jaw member 310 under the bias of living hinge 325.

Living hinge 325 may be formed from suitable materials and/or configured to define a modulus of elasticity suitable for ensuring that an appropriate grasping pressure is applied to tissue grasped between tissue-treating surfaces 314, 324 of jaw members 310, 320, respectively, in the approximated position of end effector assembly 300. In some embodiments, it may be desirable to provide a grasping pressure in the range of about 3 kg/cm$^2$ to about 16 kg/cm$^2$, although other pressures and pressure ranges are also contemplated.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 6:
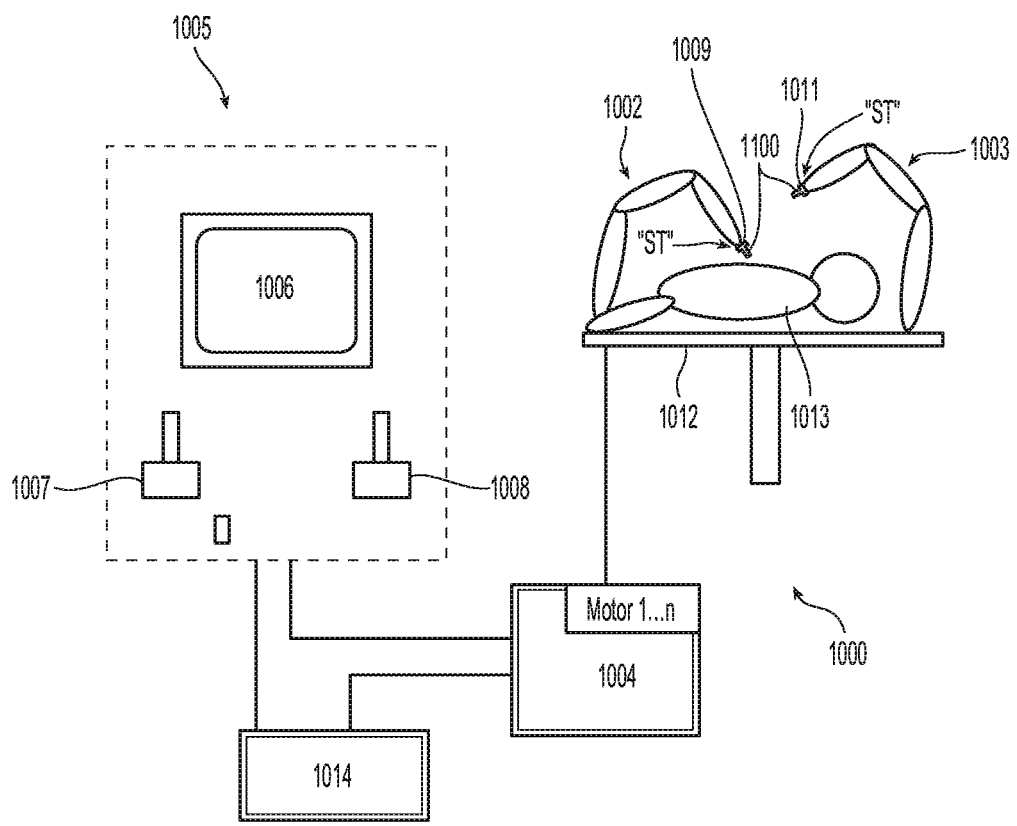
FIG. 6 is a schematic illustration of a robotic surgical system configured for use in conjunction with aspects and features of the present disclosure.

Referring to FIG. 6, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    a shaft defining an interior and a distal-most end, the shaft including a first lip and a second lip facing the first lip at the distal-most end of the shaft, each of the first lip and the second lip extending inwardly into the interior of the shaft, wherein a space is defined between the first lip and the second lip; and
    an end effector including a proximal flange extending into the interior of the shaft and a distal body extending distally from the proximal flange, the proximal flange including a notch defined therein, the notch at least partially receiving the first or second lip therein to define a fulcrum about which at least a portion of the end effector is pivotable relative to the shaft.

2. The surgical instrument according to claim 1, wherein the end effector is adapted to connect to a source of energy for supplying energy to tissue.

3. The surgical instrument according to claim 1, further including a drive bar slidably disposed within the shaft and operably coupled to the proximal flange of the end effector such that translation of the drive bar relative to the shaft pivots the at least a portion of the end effector relative to the shaft.

4. The surgical instrument according to claim 3, further including:
   a housing having the shaft extending distally therefrom; and
   a handle assembly coupled to the housing and the drive bar, the handle assembly including a movable handle selectively actuatable for translating the drive bar through the shaft.

5. The surgical instrument according to claim 1, wherein the end effector includes first and second jaw members, and wherein the first jaw member is pivotable relative to the second jaw member and the shaft about the fulcrum.

6. The surgical instrument according to claim 5, wherein the first jaw member is pivotable relative to the second jaw member between a spaced-apart position and an approximated position for grasping tissue therebetween.

7. The surgical instrument according to claim 6, wherein the first and second jaw members are adapted to connect to a source of energy for supplying energy to tissue grasped therebetween.

8. A surgical instrument, comprising:
   a shaft defining an interior and a distal-most end, the shaft including a first lip and a second lip facing the first lip at the distal-most end of the shaft, each of the first lip and the second lip extending inwardly into the interior of the shaft, wherein a space is defined between the first lip and the second lip; and
   an end effector assembly, including:
   first and second jaw members, the first jaw member including a first proximal flange and a first distal jaw body extending distally from the first proximal flange, the first proximal flange including a first notch defined therein at least partially receiving the first lip therein to define a fulcrum about which the first jaw member is pivotable relative to the second jaw member and the shaft between a spaced-apart position relative to the second jaw member and an approximated position relative to the second jaw member.

9. The surgical instrument according to claim 8, further including a drive bar slidably disposed within the shaft, the drive bar including a transverse drive pin disposed at a distal end thereof, wherein the first proximal flange further includes a cam slot defined therethrough, the transverse drive pin operably engaged within the cam slot such that translation of the drive bar relative to the shaft pivots the first and second jaw members between the spaced-apart and approximated positions.

10. The surgical instrument according to claim 9, wherein the operable engagement of the transverse drive pin within the cam slot retains the first lip at least partially within the first notch.

11. The surgical instrument according to claim 9, further including:
   a housing having the shaft extending distally therefrom; and
   a handle assembly coupled to the housing and the drive bar, the handle assembly including a movable handle selectively actuatable for translating the drive bar through the shaft.

12. The surgical instrument according to claim 8, wherein the second jaw member includes a second proximal flange and a second distal jaw body extending distally from the second proximal flange, the second proximal flange including a second notch defined therein and configured to at least partially receive the second lip to define a fulcrum about which the second jaw member is pivotable relative to the first jaw member and the shaft between the spaced-apart position and the approximated position.

13. The surgical instrument according to claim 12, wherein the first and second distal jaw bodies of the first and second jaw members define first and second tissue-treating surfaces configured to grasp tissue therebetween in the approximated position.

14. The surgical instrument according to claim 13, wherein the first and second tissue-treating surfaces are configured to conduct energy through tissue grasped therebetween to treat tissue.

* * * * *